United States Patent

Sharpe et al.

[11] Patent Number: 5,549,623
[45] Date of Patent: * Aug. 27, 1996

[54] ENDODISSECTOR SURGICAL INSTRUMENT

[75] Inventors: Leslie A. Sharpe, Edina, Minn.; Francis C. Peterson, Prescott, Wis.

[73] Assignee: Dexide, Inc., Fort Worth, Tex.

[ * ] Notice: The portion of the term of this patent subsequent to Jun. 19, 2012, has been disclaimed.

[21] Appl. No.: 93,985

[22] Filed: Jul. 19, 1993

Related U.S. Application Data

[63] Continuation of Ser. No. 793,841, Nov. 18, 1991, abandoned.

[51] Int. Cl.$^6$ ............................................. A61B 17/32
[52] U.S. Cl. ........................ 606/171; 606/166; 606/174; 128/751
[58] Field of Search ........................ 606/170, 171, 606/174, 175, 190, 110, 166, 167, 168, 169, 172, 173; 128/751, 754, 752, 753; 30/134, 135

[56] References Cited

U.S. PATENT DOCUMENTS

| | | | |
|---|---|---|---|
| 650,496 | 5/1900 | Stohlmann et al. | 606/110 |
| 1,324,976 | 12/1919 | Oesterwitz | 606/110 |
| 1,448,858 | 3/1923 | Oesterwitz | 606/110 |
| 2,541,063 | 2/1951 | Hubbard | 30/134 X |
| 3,364,572 | 1/1968 | Hoppe | 606/138 |
| 3,584,628 | 6/1971 | Green | 606/143 |
| 3,752,161 | 8/1973 | Bent | 606/169 |
| 3,802,074 | 4/1974 | Hoppe | 30/134 X |
| 3,855,699 | 12/1974 | Charlett | 30/135 |
| 4,210,146 | 7/1980 | Banko | 606/171 |
| 4,368,734 | 1/1983 | Banko | 606/170 |
| 4,499,898 | 2/1985 | Knepshield et al. | 606/170 |
| 4,516,575 | 5/1985 | Gerhard et al. | 606/170 |
| 4,577,629 | 3/1986 | Martinez | 606/171 |
| 4,656,999 | 4/1987 | Storz | 128/4 |
| 4,777,948 | 10/1988 | Wright | 606/171 |
| 4,815,465 | 3/1989 | Alvarado | 606/139 |
| 4,877,026 | 10/1989 | de Laforcade | 606/171 |
| 4,907,598 | 3/1990 | Bauer | 128/753 |
| 4,961,430 | 10/1990 | Sheahon | 606/171 X |

FOREIGN PATENT DOCUMENTS

| | | | |
|---|---|---|---|
| 2542188 | 9/1984 | France . | |
| 3543173 | 6/1986 | Germany | 606/167 |
| 0671872 | 10/1989 | Switzerland | 606/167 |
| 1331503 | 8/1987 | U.S.S.R. | 606/166 |
| 1360714 | 12/1987 | U.S.S.R. | 606/167 |

*Primary Examiner*—Christopher A. Bennett
*Attorney, Agent, or Firm*—Merchant, Gould, Smith, Edell, Welter & Schmidt

[57] ABSTRACT

A surgical cutting instrument having a surgeon operable control handle for advancing a blade over a fenestrated hook so that tissue within said fenestrated window area is dissected.

8 Claims, 5 Drawing Sheets

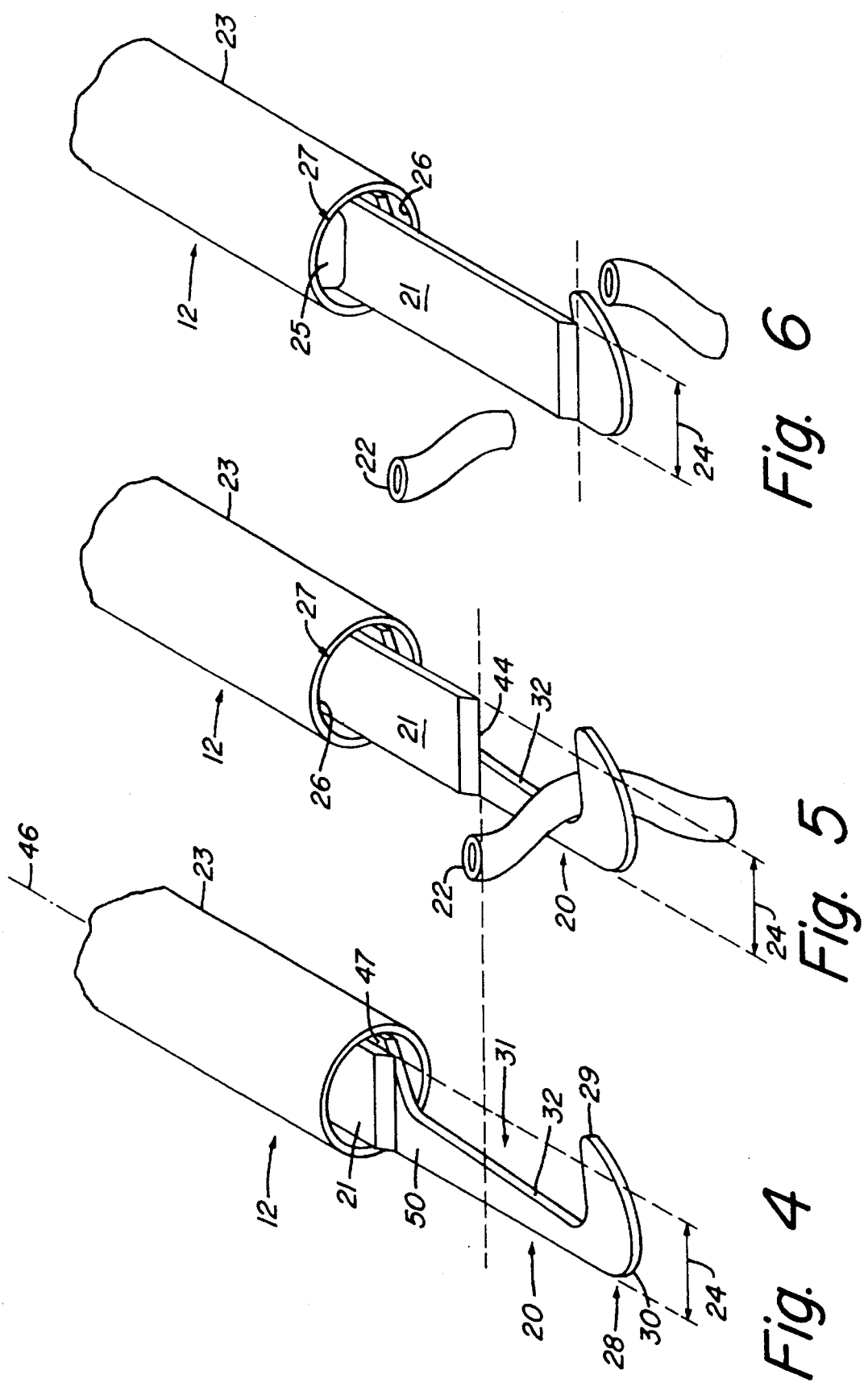

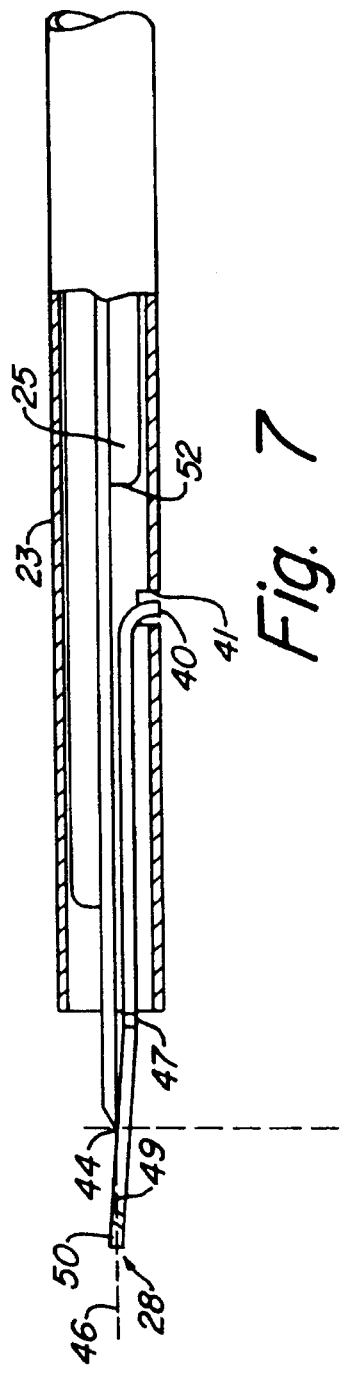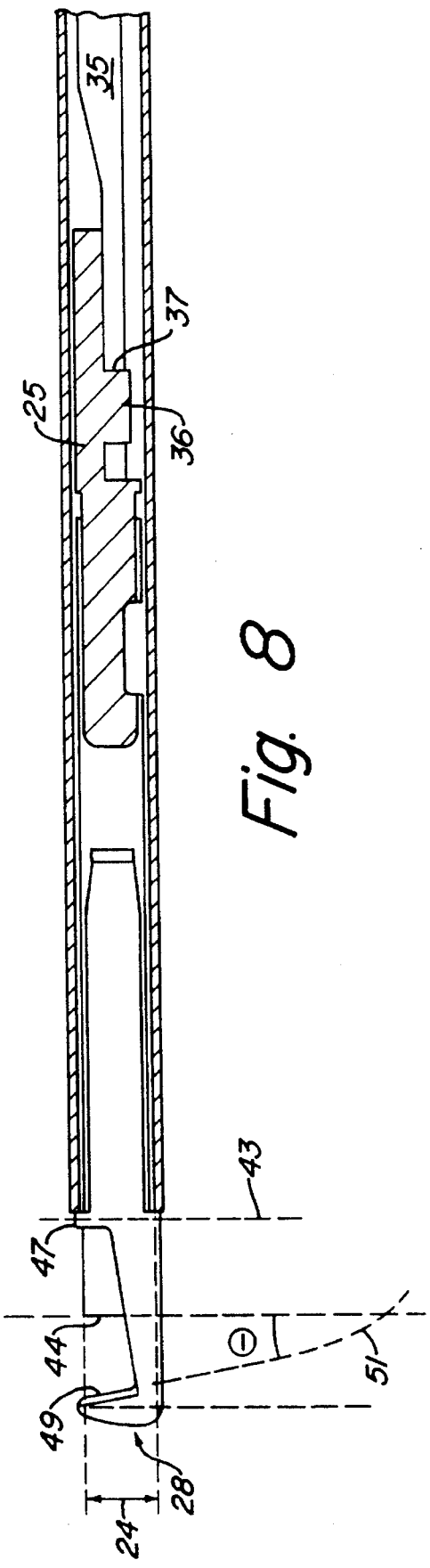

ENDODISSECTOR SURGICAL INSTRUMENT

This is a continuation of application Ser. No. 07/793,841, filed Nov. 18, 1991, now abandoned.

BACKGROUND OF THE INVENTION

The present invention relates to surgical instruments for use during laparoscopic surgery. More particularly, the invention is directed to an endoscopic dissector cutting instrument for use inside the abdominal cavity.

DESCRIPTION OF THE PRIOR ART

The typical laparoscopic surgical procedure begins with the puncture of the patient's abdominal wall and the placement of an access port. Next, gas is admitted to the abdominal cavity partially inflating it, forming a pneumoperitoneum. A laparoscope or endoscope is next inserted through the access port to permit viewing of the organs during the surgical procedure. Typically the laparoscope has both an eyepiece for direct use by the physician and a video monitor to permit visualization of the surgical field. Additional access ports may be located elsewhere on the abdominal wall to permit insertion of surgical instruments. Access ports come in a variety of diameters and 5, 7 and 11 millimeter ports are widely used for surgery within the peritoneal cavity. Instruments for insertion through such ports are readily available to practitioners and numerous surgical cutting instruments are available to surgeons specializing in these procedures.

Percutaneous surgical instruments for cutting various tissues are widely known and disclosed in a variety of contexts. Specialized instruments are available for endoscopic and laparoscopic surgeries, as well as for intraocular and biopsy procedures. See for example:

U.S. Pat. No 3,844,272 to BANKO which shows a cutting holding and tissue removal tool. In one embodiment a knife is drawn into contact with tissue by suction pressure.

U.S. Pat. No. 3,902,498 to NIEDERRER which shows a cylindrical shearing type of cutter for cutting and removing tissue.

U.S. Pat. No. 4,517,977 to FROST which shows a rotary type cutter for removal of tumorous tissue.

U.S. Pat. No. 3,995,619 to GLATZER which shows a combination instrument for probing and cutting tissue.

BRIEF DESCRIPTION OF THE DRAWING

Throughout the several figures of the drawing like reference numerals are used to identify identical structure, wherein:

FIG. 4 is a perspective view of the anterior operating portion of the instrument with the blade in the retracted position;

FIG. 5 is a perspective view of the anterior operating portion of the instrument depicting the blade moving along the hook, in an intermediate position;

FIG. 6 is a perspective view of the anterior operating portion of the instrument with the blade in the extended position;

FIG. 7 is an enlarged scale crossection of the anterior operating portion of the instrument depicting the interaction between the blade and the hook; and, FIG. 8 is an enlarged scale crossection of the anterior operating portion of the instrument depicting the interaction between the blade and the hook.

DETAILED DESCRIPTION OF THE EXEMPLARY EMBODIMENT

Figure 1:
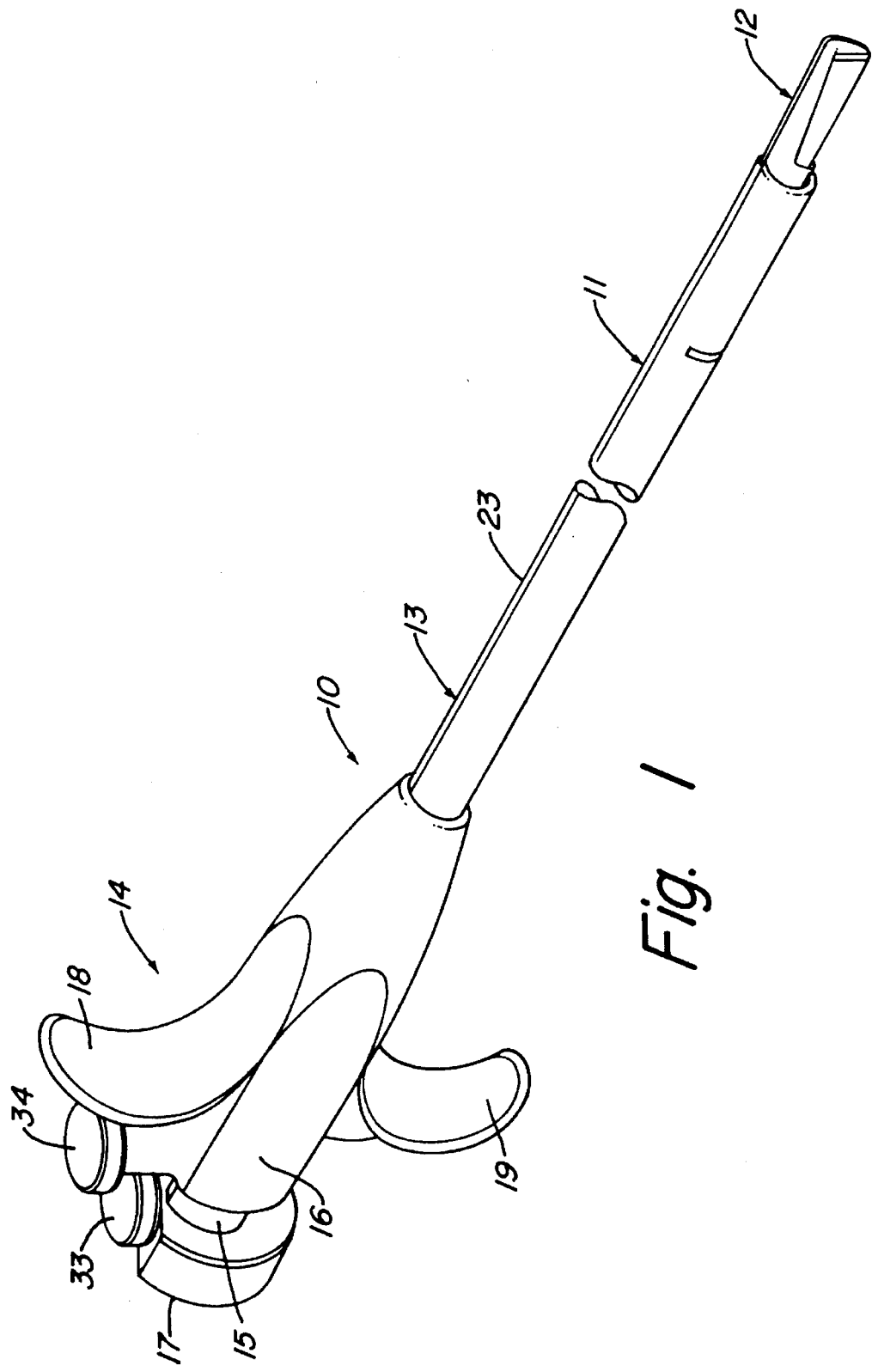
FIG. 1 is a perspective view of the assembled endodissector surgical instrument.

FIG. 1 is a perspective view of the endodissector 10. The anterior section 11 of the instrument houses the operating portion 12 of the instrument while the posterior section 13 includes the control handle structures generally designated 14. The control handle 14 is grasped by the surgeon and the anterior section 11 is inserted into the body cavity trough a suitable port. In use, the surgeon operates the control handle 14 to manipulate the operating portion 12 located on the anterior portion of the instrument. The instrument is well suited to blunt and sharp dissection of tissues as well as division of ligated tissue pedicles and the cutting of suture materials.

The control handle 14 includes a rear grip structure 15 and a foregrip structure 16. In use the rear grip 15 and foregrip 16 are squeezed together to operate the instrument. The preferred rear grip is a pommel 17, while the preferred foregrip 16 comprises a pair of complimentary loops 18 and 19. These grip structures together form a symmetrical control handle 14. This symmetrical grip arrangement makes the instrument operable with both the left and right hand. The symmetry also permits the instrument to be operated in an upright position or an inverted position when rotated through 180 degrees. The assembly screws 33 and 34 provide the surgeon with a tactile and visual reference for the orientation of the operating portion 12. The preferred semi-circular loops 18 and 19 may receive the forefinger and middle finger of the surgeon while the surgeon's thumb rests on the pommel 17. This preferred control handle 14 also can readily accept the surgeon's middle and ring finger on the loops 18 and 19 and palm on the pommel 17. This ambidextrous multi-position control handle 14 is also compact and light weight which materially aids the surgeon's control of the operating portion of the instrument. These preferred structures are preferably molded of medical grade polysulfone plastic molded onto a stainless steel sheath 23.

Figure 2:
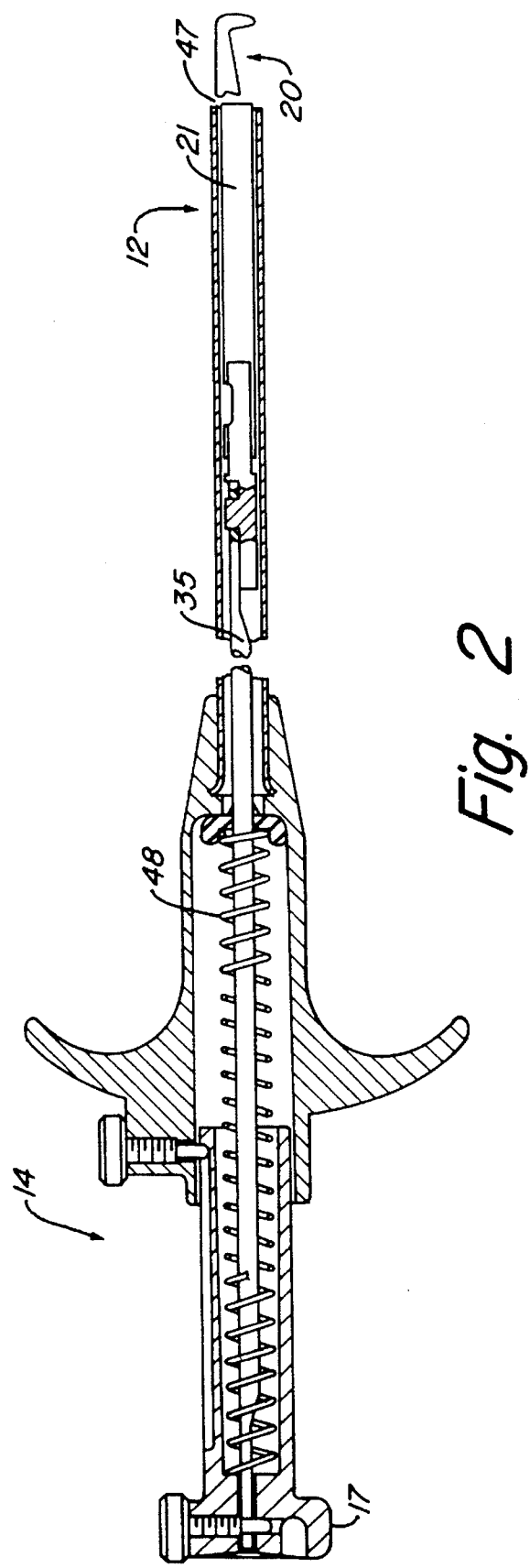
FIG. 2 is a crossection of the entire instrument depicting the control handle and the blade in the retracted position.

FIG. 2 is a crossection of the whole instrument depicting the blade in the retracted position. In the drawing, the operating portion 12 is rotated 90 degrees to better illustrate the relationship between handle 14 position and the corresponding blade 21 position. With the blade 21 in this retracted position the surgeon may use the instrument for blunt dissection. With the blade 21 in the retracted position it lies on the base 47 of the hook member 20 and is in a safe non-cutting position. The retraction spring 48 in the control handle 14 supplies spring force through the connector rod 35 to bias the blade 21 into the retracted position, when the rear grip pommel 17 is released.

Figure 3:
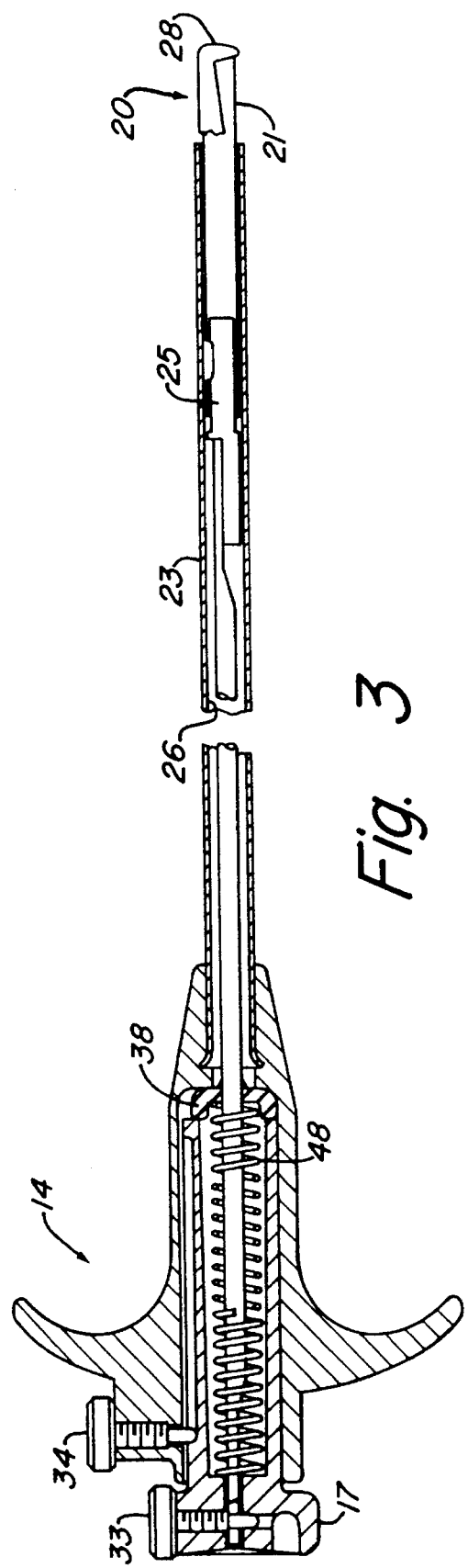
FIG. 3 is a crossection of the entire instrument depicting the control handle and the blade in the extended position.

FIG. 3 is a crossection of the whole instrument with the blade 21 and control handle 14 in the extended position. Once again the orientation of the control handle has been rotated 90 degrees to illustrate operation. With the pommel 17 fully depressed the blade 21 approaches but does not overhang the edge of the foot 28 of the hook member 20. In this extended position, the cutting blade is in a safe non-cutting position.

The crossection views show that the assembly screw 34 in the foregrip holds the rear grip 15 in the foregrip structure. Assembly screw 33 connects the rear grip 15 to one end of the connector rod 35. With the screws removed the connector rod 35 and attached blade carrier 25 can be removed from the sheath 23 by movement toward the rear. With the connector rod 35 removed the blade 21 and blade carrier 25 assembly can be detached from the connector rod 35 structure. In general the blade 21 and the carrier 25 will form a disposable assembly which is discarded after a single surgical use. Although any one of a number of connectors can be used to couple the blade 21 and blade carrier 25, the preferred connecter is a plug in slot structure described in detail later. In embodiments where the entire tool is disposable, the assembly screws may be replaced with pins preventing unauthorized disassembly.

The foregrip assembly 16 also contains a rubber gas seal 38 which encircles the circular control rod 35. This gas seal 38 prevents passage of fluid or gas through the instrument, and maintains both the pneumoperitoneum, and the sterility of the surgical field. Several elements cooperate together to improve the "feel" of the instrument. The lumen 26 of the sheath 23 is drawn stainless steel tubing with tightly controlled interior diameter and smoothness. It is preferred to form the disposable blade carrier 25 from a self lubricating plastic material, such as polypropylene. Where the entire instrument is disposable it is preferred to use medical grade polysulfone for the plastic blade carrier. Together the lumen 26 and carrier 25 reduce the friction and stiction associated with blade movement, this permits the use of a relatively low force retraction spring 48 improving the tactile feedback to the surgeon.

FIGS. 4 through 6 are directed to the operating portion 12 of the instrument which includes a "hook" 20 and "blade" 21. In FIG. 4 the blade 21 is in the retracted position while FIG. 6 shows the blade 21 in the fully extended position. In FIG. 5 the blade 21 is shown in an intermediate position advancing toward an anatomical structure 22, which has been dissected in FIG. 6. It is important to note that the cutting edge 44 of blade 21 is unexposed in both the retracted position of FIG. 4 and the extended position of FIG. 6 improving safety.

The blade 21 is preferably located along the central axis or centerline 46 of the sheath 23 to maximize its width 24, and to minimizes bending moments on the blade carrier 25. The blade 21 is relatively thick to maximize its stiffness, and is preferably made of a hardened stainless steel alloy, prototype tools have been hardened to 50–53 RC Rockwell. The blade 21 itself is supported in a plastic carrier 25 which acts as a bearing to locate and guide the blade 21 in the lumen 26 of the sheath 23. A portion of this carrier 25 is visible in the mouth 27 of the sheath 23 as shown in FIG. 6.

The hook 20 has a complex shape and it is made from a relatively thin and flexible material, prototype tools have used hardened stainless steel hardened to 50–53 Rockwell. The hook 20 alone can be used for blunt dissection of tissue planes and as a probe to explore elevate and visualize tissue masses. It is important for the surgeon to be able to accomplish these blunt dissections with the same tool that is used for cutting or sharp dissection to enhance the speed and safety of the surgical procedure. For improved safety and utility the hook has smooth and rounded surfaces at those locations where the hook is likely to contact tissue. For example the foot portion 28 of the hook 20 has a blunt toe 29 area and a blunt heel area 30. The hook 20 also has a fenestrated window area 31 bounded by the edge of the blade and the inner edge 32 of the hook 20. The exact fenestration does not appear critical. However, it is desirable to have a relatively large and asymmetric window so that a small number of cuts are required to dissect large structures. This requirement must be balanced against the requirement of having sufficient land area to form an adequate line of contact along the upper surface 50 of the hook 20 surface to guide the blade onto the foot 28.

FIG. 7 and FIG. 8 should be considered together. In these drawings the hook 20 and blade 21 assembly are shown in an enlarged scale to emphasize the geometry of the hook 20. The hook has a formed tang 40 which is inserted into a complimentary notch 41 in the tubular sheath 23 to anchor the hook 20 to the sheath 23. In use, the blade 21 and blade carrier 25 will lie over the tang 40 and prevent it for becoming disengaged from the sheath 23. The blade carrier 25 will also bottom out on this tang 40 to limit blade motion and to define the extended position. This ensures that tolerance stacking in the sheath 23 and handle structure 14 does not cause the blade edge 44 to overhang the foot 28 in the extended position. The tang 40 portion must be narrow to permit engagement with the sheath 23 while the base 47 of the hook must be substantially as wide as the sheath 23 to support and stabilize the hook 20 near the center of the lumen 26. When the blade is fully retracted it is preferred that the blade edge be fully supported by the base 47 of the hook 20 as indicated by the reference line 43 in FIG. 8. In this position the retracted blade 21 provides additional support for the hook 20 against torsional loads resulting from rotation of the hook 20 against anatomical structures. This additional support improves the "feel" of the instrument.

The preferred method of connecting the blade carrier 25 to the control rod 35 is depicted in FIG. 8 where the oblong plug 36 which is molded in the carrier 25, engages the complimentary slot 37 formed in the control rod 35.

In FIG. 7 the hook 20 is curved upwardly past the center line 46 of the sheath 23. This exaggerated curve demonstrates that only the edge 44 of the blade 21 is touching the upper surface 50 of the hook 20 as indicated by position line 45. The pressure on this line of contact enhances the cutting action of the blade edge 44 as it overlaps the complimentary cutting edge 49 of the foot 28. It is preferred that the cutting edge 49 of the foot 28, be substantially sharp at an acute angle to the upper surface 50 of the hook. It is also preferred that the included angle between to edge of the foot 49 shown as line 51 and the edge of the blade 44 shown as line 45 be approximately 10 degrees as shown by angle theta. It is preferred that the included angle be achieved with a skewed foot edge depicted by line 51 and an orthogonal blade edge 44, depicted by line 45.

It is preferred to limit blade 21 extension by having a portion 52 of the blade carrier 25 bottom out on the tang 40 which mounts the hook 20 in the sheath 23.

What is claimed:

1. A surgical cutting tool for dissecting tissues comprising:

an anterior section having an operating portion;

a posterior section having a control handle;

a cylindrical sheath extending between said anterior section and said posterior section, connecting said control handle to said operating portion, said sheath having a lumen, said lumen having a central axis;

a connector rod positioned within said lumen for transferring motion from said control handle to said operating portion;

a blade located in said lumen connected to said connector rod whereby manipulation of said control handle moves said blade within said lumen, along the axial length of said lumen, from a first position wherein said blade lies on the base (47) of a fenestrated hook member (20) disabling said blade from cutting, to a second position wherein said blade lies on the surface of said fenestrated hook member, disabling said blade from cutting, said blade having a width less than or equal to the widths of said base and said surface of said fenestrated hook member;

said fenestrated hook member connected to said sheath and extending from said sheath, said hook member for contacting and supporting said blade along a line of contact during blade motion, said hook member adapted to be deflected by said blade, during blade motion, whereby said hook member and said blade form a tissue cutting means for dissecting the tissue.

2. The surgical cutting tool of claim 1 wherein said fenestrated hook member comprises:

a leg member extending a distance axially from the distal end of said sheath, and having an upper blade support surface for guiding said blade, said upper support surface being narrower than the width of said blade;

a foot member at the terminal end of said leg member, said foot member being substantially as wide as said sheath, said foot member having a rounded and blunt heel member and a rounded and blunt toe member;

said leg member and said foot member together defining a tissue reception window;

whereby tissue in said window is cut as said blade overlaps said foot member in response to motion imparted by said control handle.

3. The surgical cutting tool of claim 2 wherein:

said blade having a blade edge forming a blade edge angle with said central axis of said sheath;

said foot having a substantially linear cutting edge formed in opposing position to said blade edge, forming a foot angle with said central axis of said sheath;

wherein said foot angle and said blade angle are not the same value.

4. The surgical cutting tool of claim 2 wherein:

said blade having a blade edge forming a blade edge angle with said central axis of said sheath;

said foot having a substantially linear cutting edge formed in opposing position to said blade edge, forming a foot angle with said central axis of said sheath;

wherein said foot angle and said blade angle differ by an amount greater than 8 degrees and less than 16 degrees.

5. The surgical cutting tool of claim 1 wherein said control handle comprises:

a rear grip, having a central axis, and attached to said connector rod;

a foregrip having a central axis adapted to engage and receive said rear grip along said central axis such that said rear grip can reciprocate in said foregrip;

a retraction spring located in said foregrip and coupled to said rear grip such that said rear grip is biased into a first retracted position.

6. The surgical cutting tool of claim 5 wherein said foregrip comprises:

a pair of semicircular loops.

7. The surgical cutting tool of claim 5 wherein said rear grip comprises:

a pommel.

8. A surgical cutting tool for dissecting tissues comprising:

an anterior section having an operating portion;

a posterior control handle, having a rear grip, aligned along a central axis;

a foregrip aligned along said central axis adapted to engage and receive said rear grip along said central axis such that said rear grip can reciprocate in said foregrip;

a retraction spring located in said foregrip and coupled to said rear grip such that said rear grip is biased into a first retracted position;

a cylindrical sheath extending between said anterior section and said posterior control handle, connecting said control handle to said operating portion, said sheath having a lumen, said lumen aligned along said central axis;

a connector rod positioned within said lumen for transferring motion from said control handle to said operating portion;

a blade located in said lumen, supported by a blade carrier, said blade carrier being connected to said connector rod whereby manipulation of said control handle moves said blade within said lumen, along the axial length of said lumen, between a first position wherein said blade is retracted onto a first surface of a fenestrated hook member disabling the cutting surface of said blade and a second position wherein said blade overlays a second surface of said fenestrated hook member disabling the cutting surface of said blade, said blade having a width less than or equal to the widths of said first and second surfaces of said fenestrated hook member;

said fenestrated hook member connected to said sheath and extending from said sheath, said hook member for contacting and supporting said blade during blade motion;

said blade and said fenestrated hook member forming said operating portion;

wherein said hook member and said blade form a tissue cutting means for dissecting said tissue, when said foregrip and said rear grip are pressed together compressing said retraction spring, and whereby abutment of said blade carrier against said fenestrated hook member limits travel of said blade defining said second extended position.

* * * * *